Figure 1:
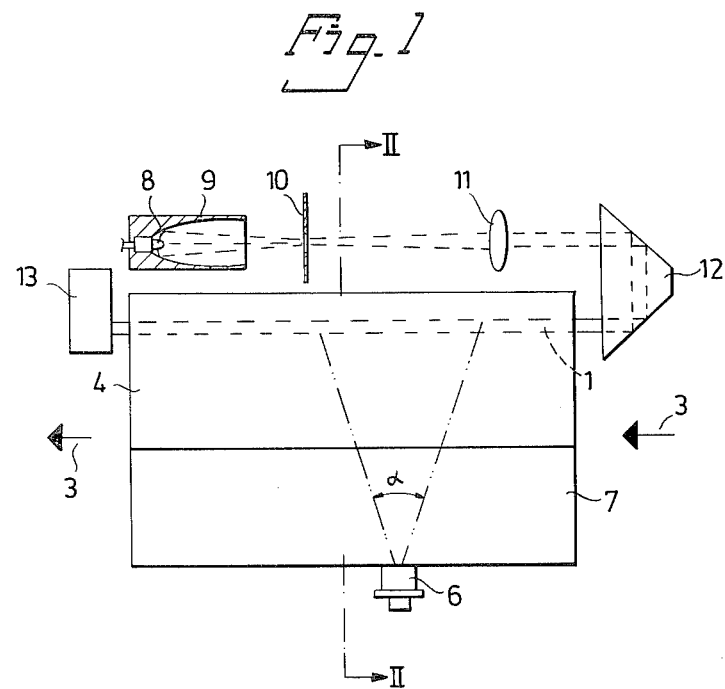

United States Patent [19]

Källander

[11] 4,245,910
[45] Jan. 20, 1981

[54] APPARATUS FOR DETECTING PARTICLES SUSPENDED IN A GAS

[75] Inventor: Stefan Källander, Lidingö, Sweden

[73] Assignee: Svenska Utvecklings Aktiebolaget, Stockholm, Sweden

[21] Appl. No.: 125,025

[22] Filed: Feb. 27, 1980

[30] Foreign Application Priority Data

Mar. 7, 1979 [SE] Sweden .................................. 7902054

[51] Int. Cl.³ .................... G01N 15/06; G01N 21/51
[52] U.S. Cl. .................................. 356/338; 250/574; 340/627
[58] Field of Search ................................ 356/337–340, 356/343; 250/574; 340/628, 630, 627; 350/293

[56] References Cited

U.S. PATENT DOCUMENTS 3,946,239    3/1976    Salzman et al. ................... 356/39 X

FOREIGN PATENT DOCUMENTS 1931631  1/1971  Fed. Rep. of Germany.
7713459  7/1979  Sweden .................................. 356/338

OTHER PUBLICATIONS

Cecchi, D. R. et al., "Elliptical Light Collector", IBM Technical Disclosure Bulletin, vol. 13, No. 11, Apr. 1971, p. 3327.

Moenke-Blankenburg et al., "New Aspects of the Apparatus, Technique and the Methods of Laser Micro-Emission Analysis" Spectrochimica Acta, vol. 30B, pp. 227–234.

Primary Examiner—John K. Corbin
Assistant Examiner—Bruce Y. Arnold
Attorney, Agent, or Firm—Browdy and Neimark

[57] ABSTRACT

The invention relates to a dust indicator for detecting the presence of suspended particles, either solid or liquid, in a gas. A concentrated, substantially parallel light beam (1) of suitable wavelength is directed through a measuring chamber (2) containing the gas to be examined. The light beam is surrounded by an internally reflecting elliptical cylindrical reflector (4) in a manner such that the beam (1) coincides with one focal axis ($B_1$) of the reflector. Arranged in the other focal axis ($B_2$) of the reflector (4) is at least one light detector (6) with its active surface facing the reflector and the center axis of its field of view directed, preferably perpendicularly, towards the first said focal axis ($B_1$) along which the beam (1) is directed.

5 Claims, 2 Drawing Figures

APPARATUS FOR DETECTING PARTICLES SUSPENDED IN A GAS

The present invention relates to apparatus for detecting the presence of solid or liquid particles suspended in a gas, i.e. aerosols.

The increasing interest in environmental conditions, and in particular in the conditions of working environments, has, inter alia, meant an increased requirement of instruments which, in addition to being capable of detecting the presence of gas-suspended solid or liquid particles, e.g. dust, smoke particles and fine droplets of liquid, such as oil, shall also be capable of measuring, or at least estimating, the concentration of said particles in said gas. Such instruments can be used, for example, to monitor the air present in a room or at a working site with respect to the presence of harmful impurities in the form of solid or liquid particles. They can also be used for checking or monitoring the efficiency of filter systems and other purification systems used for treating and purifying air which is to be passed to a working location. It is also possible to use instruments of this kind as smoke detectors and in fire-warning systems.

Instruments and apparatus for the above mentioned purpose have previously been proposed and sold, in which instruments a volume of the gas to be examined is transilluminated with a concentrated optical beam, the particles present in the transilluminated volume of gas causing a scattering of the radiation in the beam and said scattered radiation acting upon a radiation detector, the output signal of which is used as an indication and as a measurement of the presence of suspended particles in the gas being examined. By optical beam or radiation is meant here radiation both within and outside the range of visible light, for example within the infra-red wave-band. Different embodiments of such instruments are generally described in, for example, the Swedish Pat. Spec. No. 350,604, German Published Patent Applications Nos. 2,051,546, 2,260,150, 2,260,313, and U.S. Pat. Spec. Nos. 3,281,748, 3,248,551, 3,914,616.

The previously proposed and retailed instruments based on the afore-described light-scattering principle are, however, unsatisfactory in certain respects, and in particular with regard to their sensitivity. This is because the scattered radiation has a very low intensity in relation to the intensity of the primary, transilluminating beam. The intensity of the scattered radiation is a function of the size and shape of the particles and varies strongly in different directions relative to the direction of the primary beam. In order to obtain a high degree of sensitivity with respect to a given particle size it is thus necessary that the radiation scattered by the particles within the transilluminated volume of gas can be collected within a well-defined angular range relative to the direction of the primary beam, and at the same time from the greatest possible volume of gas and over the greatest possible part of the circumference of the primary beam, and be caused to act upon the radiation detector used for measuring the intensity of the scattered radiation. At the same time, however, the radiation detector must be effectively screened so that it is not influenced directly by the radiation from the primary, transilluminating beam or by any external radiation, such as daylight or other forms of light entering into the instrument. Those instruments known hitherto are unable to fulfill all of these conditions satisfactorily.

Consequently, the object of the invention is to provide an improved apparatus working on the light-scattering principle for detecting the presence of gas-suspended particles, said apparatus being able to satisfy the aforementioned conditions more completely than the previously known apparatus.

This object is achieved by an apparatus having the features disclosed in the accompanying claims.

As a result of the special design of the reflector of the apparatus according to the invention, the radiation scattered by the particles in the volume of gas transilluminated by the primary beam is collected over a very large part of the circumference of the primary beam and is caused to act upon the beam detector via one single reflection in the reflector. In this way, a substantially larger portion of the scattered radiation will be passed to the radiation detector. Further, the scattered radiation can be readily collected, and measured, from a considerable length of the primary beam, i.e. from a large volume of transilluminated gas. This is particularly possible when, in accordance with one embodiment of the invention, there is arranged a plurality of radiation detectors in side-by-side relationship along one focal axis of the reflector. The apparatus obtains a high degree of sensitivity in this way, and a high signal-noise-ratio. The design of the reflector also ensures that the radiation detector will not be activated by any direct radiation from the primary, transilluminating beam. It is also relatively easy to screen the radiation detector from any external light which may enter the instrument.

Figure 2:
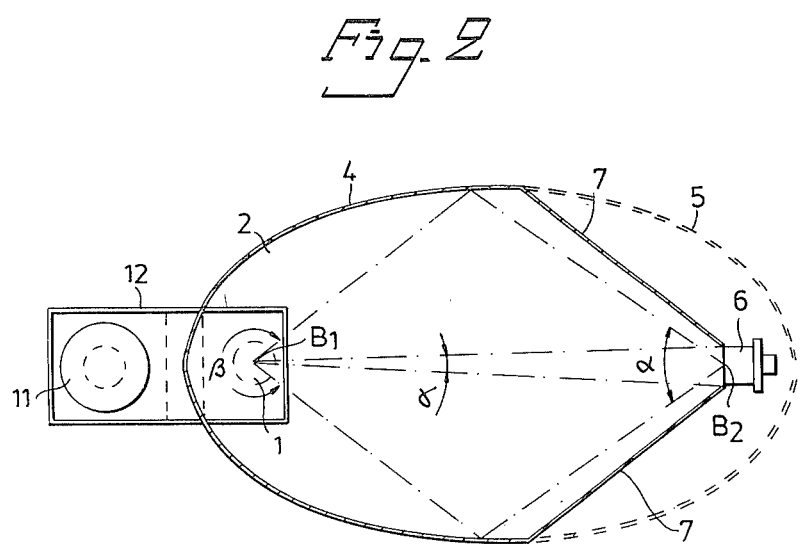

The invention will now be described in more detail with reference to the accompanying schematic drawing, in which FIG. 1 is a plan view of the principle design of an exemplary embodiment of an apparatus according to the invention; and FIG. 2 is a sectional view in larger scale of the apparatus in FIG. 1, taken on the line II-II in FIG. 1.

The exemplary and schematically illustrated apparatus according to the invention comprises means for generating a concentrated, substantially parallel beam of radiation 1, which is directed through a measuring chamber 2 containing the gas whose content of suspended particles shall be determined. In the illustrated embodiment it is assumed that said measuring chamber 2 is open at both ends thereof, so that the gas in question can flow therethrough, as illustrated by means of arrows 3 in FIG. 1. That part of the beam 1 extending through the chamber 2 is surrounded by a reflector 4, which also forms part of the chamber walls. In the illustrated embodiment, the reflector 4 is shaped as a part of an internally reflecting, elliptical cylindrical surface. The remaining part of the elliptical cylindrical surface is indicated in FIG. 2 by a dash line 5. Thus, the reflector 4 consists of a part of an elliptical cylindrical surface which is cut away along a plane extending parallel with the plane of the minor axis of the elliptical cross-section of the cylinder. The reflector 4 is so arranged relative to the beam 1 that the centre axis of said beam coincides with one focal axis $B_1$ of the elliptical cylindrical surface. It will be seen herefrom that, consequently, the radiation scattered by the particles in the volume of gas transilluminated by the beam 1 will be reflected by the reflector 4, towards the other focal axis $B_2$ of the elliptical cylindrical surface. Arranged on this focal axis is a photo-detector 6, such as a photo-diode, with its active surface and its field of view facing the reflector 4, to advantage in a manner such that the centre axis of the field of view of the detector 6 is directed towards the focal axis $B_1$, i.e. lies in the plane of the major axis of the elliptical cross-section of said elliptical cylinder, and is substantially perpendicular to the focal axis $B_1$ and therewith to the direction of the beam 1. The angle of the field of view of the radiation detector 6 has been referenced $\alpha$ in FIG. 2. As will be understood, the elliptical cylindrical reflector 4 shall be dimensioned so that the whole of the field of view of the detector 6 is covered by the reflector. It will also be understood that the light scattered within the angular range $\beta$ by particles in said gas volume within the beam 1 will be directed onto the active surface of the detector 6 after being reflected only once by the reflector 4. In addition, of course, scattered light within the angular range $\gamma$ will impinge on the active surface of the detector 6 without any reflection by the reflector 4. Consequently, the detector 6 will receive a very large part of the total light scattered by the particles suspended in the volume of gas transilluminated by the beam 1, thereby providing a high degree of sensitivity and a high signal noise ratio. The detector 6 can also receive light scattered from particles within a considerable part of the length of the beam 1, as illustrated in FIG. 1, where the angle of the field of view of the detector 6 is also referenced $\alpha$. If it is desired to receive and to measure light scattered from particles within a still larger part of the length of the beam 1, this can readily be achieved by arranging a plurality of beam detectors in side-by-side relationship along the focal axis $B_2$.

The remaining part of the wall of the measuring chamber 2, which is formed as a through-flow passage for the gas, is referenced 7 in the drawing and can, in principle, have any desired form. The radiation detector 6 can advantageously be arranged in an opening in the wall 7. Suitably, the inner surface of the wall 7 is non-reflecting, i.e. a dull, black surface.

In the illustrated embodiment of the apparatus according to the invention, the beam 1 is generated by means of a light source in the form of a light emitting diode 8 arranged in one focal point of an ellipsoidal reflector 9 operative to collect the radiation from the diode 8 within a large solid angle and to concentrate the radiation onto a small surface at the other focal point of the ellipsoidal reflector, in which other focal point the aperture of an aperture means 10 is placed. A lense system 11 collects the light passing through the aperture 10 to form a well collimated light beam, which is directed via a reflecting prism 12 into the measuring chamber 2, as the light beam 1 along the focal axis $B_1$ of the elliptic cylinder reflector 4. Arranged at the other end of the reflector 4 is a radiation trap 13, in which the beam 1 is caught and extinguished. This radiation trap may be of any suitable design. Because the means required for generating the beam 1 are arranged on the outside of the reflector 4 in the describe manner, the advantage is obtained that the total axial length of the apparatus is limited to correspond substantially to the axial length of the reflector 4. It will be understood, however, that in an apparatus according to the invention the beam of radiation passing through the measuring chamber radially inwardly of the reflector can also be generated in another way and by means arranged in a manner different to that described.

Other modificatins are also possible within the scope of the claims.

I claim:

1. An apparatus for detecting the presence of solid or liquid particles suspended in a gas, comprising a measuring chamber for receiving the gas to be examined; means for generating a concentrated, substantially parallel beam of optical radiation having a center axis and for directing said beam through said measuring chamber; a reflector having a reflector surface consisting of at least a part of an internally reflecting, elliptical cylindrical surface, so arranged that the centre axis of said beam substantially coincides with one focal axis of said elliptical cylindrical reflector surface; and a radiation detector arranged with its active surface located substantially tangent to the other focal axis of said elliptical cylindrical surface and with the centre axis of its field of view directed onto said beam and located substantially in the same plane as the major axis of the elliptical cross-section of said elliptical cylindrical surface.

2. An apparatus as claimed in claim 1, wherein said reflector surface consists of a part of said elliptical cylindrical surface cut-away along a plane located between the two focal axes and parallel with the plane of the minor axis of the elliptical cross-section of the elliptical cylindrical surface, the location of said first-mentioned plane being such that the reflector surface effectively covers the whole of the field of view of the radiation detector.

3. An apparatus as claimed in claim 1, wherein said radiation detector is arranged with the centre axis of its field of view directed substantially perpendicularly to the direction of said beam.

4. An apparatus as claimed in claim 1, wherein said reflector surface forms part of an outer wall of said measuring chamber, which is arranged to be through-passed by the gas being examined substantially parallel with the direction of said beam.

5. An apparatus as claimed in claim 1 comprising a plurality of radiation detectors arranged in side-by-side relationship along said other focal axis.

* * * * *